US00PP29211P2

(12) United States Plant Patent
Hansen

(10) Patent No.: US PP29,211 P2
(45) Date of Patent: Apr. 3, 2018

(54) ***SEDUM* PLANT NAMED 'NIGHT EMBERS'**

(50) Latin Name: ***Sedum* hybrid**
Varietal Denomination: Night Embers

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/530,536

(22) Filed: Jan. 25, 2017

(51) Int. Cl.
*A01H 5/02* (2018.01)

(52) U.S. Cl.
USPC ..... Plt./479

(58) Field of Classification Search
USPC ..... Plt./479
See application file for complete search history.

*Primary Examiner* — Annette H Para

(57) ABSTRACT

The new and distinct cultivar of perennial *Sedum* plant named 'Night Embers' is characterized by tight-forming compact clumps, flower stems that resist falling over and opening up in the center of the plant throughout the growing season, medium-sized black-purple, semi-glossy foliage and numerous mauve-pink flowers clustered on huge heads completely covering the plant, useful for landscaping as a specimen plant, container plant, en masse or as a cut flower.

1 Drawing Sheet

Figure 1:
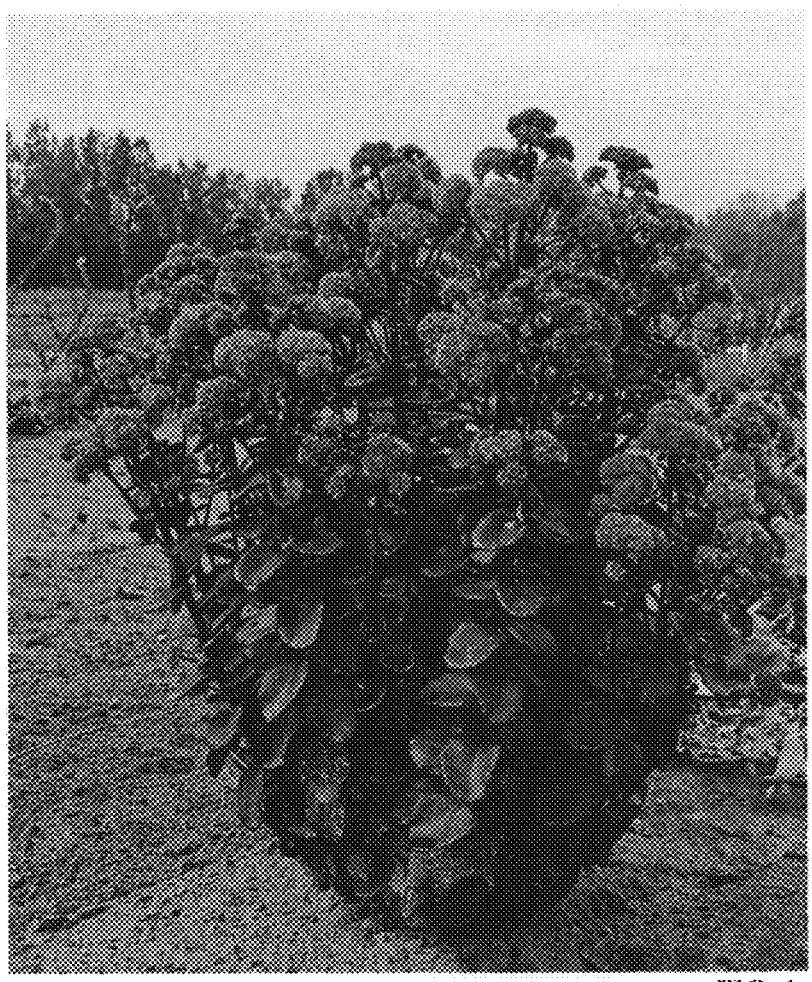
Figure 2:
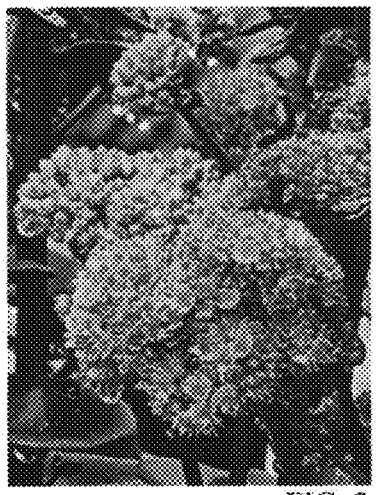

Botanical designation: *Sedum* hybrid.
Cultivar denomination: 'Night Embers'.

BACKGROUND OF THE INVENTION

The present invention relates to a new and distinct cultivar of *Sedum* plant, botanically known as *Sedum* and hereinafter referred to by the cultivar name 'Night Embers'. There are over 300 recognized species of the genus *Sedum*.

The new *Sedum* plant is a selection of a planned breeding program conducted by the inventor, at a wholesale perennial nursery in Zeeland, Mich., USA.

The new *Sedum* plant originated as a single seedling from a cross in the summer of 2012 between the unreleased proprietary hybrid K9-123-01 (not patented) as the female or pod parent and an unspecified sibling to K9-123-01 as the male or pollen parent. *Sedum* 'Night Embers' was assigned the breeder code number 12-50-5 to keep it separated from among thousands of other seedlings of this and other crosses when it progressed through the initial trial phase in the summer of 2013. The selected single seedling clone was originally was selected for it strong, healthy, upright growth, colorful foliage and flowers.

Asexual reproduction of *Sedum* 'Night Embers' by vegetative cuttings at a wholesale perennial nursery in Zeeland, Mich., USA since the summer of 2013, has shown that the unique features of this new *Sedum* plant are stable and reproduced true to type in successive generations.

SUMMARY OF THE INVENTION

Plants of *Sedum* 'Night Embers' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Night Embers'. The following characteristics in combination distinguish 'Night Embers' as a new and distinct autumn stonecrop plant unique from all other autumn stonecrop plants known to the inventor:

1. Tight-forming compact clumps with vertical stems.
2. Stems remain erect in the center of the plant throughout the growing season.
3. Medium-sized, black-purple, semi-glossy foliage.
4. Numerous branched stems produce flower clusters of mauve-pink completely cover the top of the plant.

In comparison to the female and male parents, the new plant retains its upright stems better through the entire growing season. The nearest comparison variety known to the inventor is 'Black Jack' U.S. Plant Pat. No. 16,736. The new plant better maintains foliage completely to bottom of stem and is taller than 'Black Jack'. Compared with 'Desert Black' U.S. Plant Pat. No. 24,902 the new plant is taller, with more stiffly upright stems, larger leaves and darker foliage. Compared with 'Chocolate Cherry' U.S. Plant Pat. No. 24,970 the new plant is taller and produces more upright stems. Compared with 'Touchdown Teak' U.S. Plant Pat. No. 26,078 the new plant is taller, more upright and produces foliage of a more greyed-purple and less reddish brown.

BRIEF DESCRIPTION OF THE PHOTOGRAPH

The photograph of the new plant demonstrates the unique traits and the overall appearance of *Sedum* 'Night Embers'. The colors are as accurate as reasonably possible with color reproductions of this type. Variations in ambient light spectrum, source and direction may cause the appearance of minor variation in color. The plants used in the photograph were two-year old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

The following is a detailed description of two year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2001 edition of The Royal Horticultural Society Colour Chart except where general color dictionary terms are used.

Botanical designation: *Sedum* hybrid;

Cultivar denomination: 'Night Embers';

Parentage: K9-123-01 (not patented) female, or seed, parent; unspecified sibling to K9-123-01 (not patented) male or pollen parent;

Asexual propagation: Stem tip cuttings and division;

Time to initiate roots: About two weeks;

Time to finish a 3.7 liter flowering container: About three months in the summer from a rooted 2.5 cm plug;

Root description: Thick, fleshy; freely branching; creamy white to light tan in color.

Plant habit: Winter-hardy herbaceous perennial; clumping, upright mound; stems stiff and upright arising from a dense crown; flower heads freely branching; dense and full, not opening in center later in the season;

Growth rate: Moderately vigorous;

Plant size: About 65.0 cm tall and 61.0 cm wide in full flower;

Main stems: Terete, glaucous, glabrous; diameter at base about 6.0 mm, about 42 cm long from base to initial branches; maintaining foliage to the ground; internodes average about 2.0 cm; about 18 stems per plant;

Main stem color: Nearest RHS 138A suffused with nearest RHS 184A in proximal portion and between RHS 187A and RHS N187A in distal region;

Lateral branches: Glaucous; primary branches about 3.5 mm diameter and about 9.5 cm long;

Lateral branch color: Between RHS 187B and RHS 187C;

Foliage: Ovate-orbicular; alternate, simple, smooth, glabrous, glaucous; sessile; thick, fleshy and succulent; apex bluntly acute; base truncate; margin irregularly and shallowly dentate, primarily in distal one half of leaf, about 1.0 cm apart; average about 6.7 cm long, about 6.2 cm across and about 1.5 mm thick at base, decreasing in size distally; attitude outward;

Foliage color: Adaxial surface between RHS N187A and RHS 187A with base nearest RHS 137A, abaxial surface between RHS 189A and RHS 137A with tinting of nearest RHS 187A;

Venation: Pinnate; color abaxial midrib nearest RHS 146D, adaxial midrib and secondary veins color same as surrounding leaf tissue on both surfaces;

Flower: Stellate, actinomophic; pentamerous; persistent; attitude upright to outwardly in terminal compound cymes; about 7.0 mm across and 4.0 mm deep;

Fragrance: None detected;

Flowering season: Beginning late August to late September in Zeeland, Mich.; able to be forced to flower in greenhouse out of season with about 2 months of growth following 9 weeks of vernalization;

Longevity: Flower cymes remain effective for about three weeks on the plant and one week as cut flowers; individual flowers persistent;

Flower buds about one day prior to opening: Broadly ellipsoidal; apex broadly acute; base rounded; about 3.0 mm diameter and about 3.5 mm long; shallowly longitudinally sulcate;

Flower bud color: Longitudinally striped alternately with between RHS 150D and RHS 145C and nearest RHS 187B;

Inflorescence: About 13.9 cm tall from first branch and about 15.4 cm across; up to about 150 flowers per branch and about 800 to 1200 per inflorescence;

Petals: Typically five, broadly-lanceolate; acute apex, base fused, margin entire; glabrous abaxial and adaxial; typically 4.0 mm long and about 2.0 mm across at fusion;

Petal color: Adaxial lighter than RHS N155D with basal 1.0 mm lighter than RHS 60D, abaxial maculate or notate with nearest RHS 187C and midrib of nearest RHS 139D;

Calyx: With five sepals, fused at base; adpressed to petals, about 1.5 mm long and about 2.5 mm diameter;

Sepals: Campanulate; lanceolate; margin entire; glabrous and slightly glaucous both abaxial and adaxial; acute apex, fused at the base; about 1.5 mm long and about 1.0 mm wide at fused base;

Sepal color: Abaxial and adaxial nearest RHS 137B, maculate or notate with nearest RHS 187B;

Peduncles: Terete; slightly glaucous, glabrous; strong and stiff, yet flexible; freely branching; erect in center with branches to about 45 degrees from perpendicular; about 20 cm long and 5.0 mm diameter;

Peduncle color: Nearest RHS 187A;

Pedicels: Terete; glabrous, slightly glaucous; strong and stiff, yet flexible; about 3.0 mm long and 0.7 mm diameter;

Pedicel color: Nearest RHS 137B and maculate or notate with nearest RHS 187B;

Androecium: Typically ten stamens;

*Filaments*.—Outwardly; about 3.8 mm long and about 0.2 mm diameter; color white to transparent.

*Anthers*.—Basifixed, longitudinal; globose to ellipsoid; about 0.7 mm long and 0.6 mm diameter; color nearest RHS N30A.

*Pollen*.—Moderate in quantity; color nearest RHS 18B.

Gynoecium: Typically five; cylindrical, conic in distal one third; about 4.0 mm long and 1.0 mm diameter;

*Style*.—Terete; about 0.5 mm long and 0.5 mm diameter at point of attachment to ovary; glabrous; color nearest RHS 60C.

*Stigma*.—Minute, globose; about 0.2 mm diameter and 0.2 mm long; color nearest RHS N155C.

*Ovary*.—Nearly terete, tapering at apex to style; about 3.0 mm long and 1.0 mm diameter; color nearest RHS 181D when first opening and nearest RHS 187C when pollen dehisced.

Fruit: Ventrally dehiscent follicle; about 3.0 mm long and 3.0 mm across; color at maturity nearest RHS 177A;

Seed: Sparse; fine; lanceolate; about 1.0 mm long and less than 0.2 mm across; color between RHS 165A and RHS 165B;

Disease and pest resistance: Plants of the new *Sedum* 'Night Embers' grow best with good drainage, full sun and moderate to low fertility. 'Night Embers' is cold hardy from USDA zones 3 to 9 and has tolerated temperatures of at least 35 degrees C. 'Night Embers' tolerates heavy rains and wind and is not prone to develop an open center later in the season as many other *Sedum* cultivars do. Other pest and disease resistance and tolerance outside that normal for *Sedum* is not known.

It is claimed:

1. The new and distinct perennial *Sedum* plant named 'Night Embers' as herein described and illustrated.

* * * * *